United States Patent
Shah

(10) Patent No.: US 9,987,012 B2
(45) Date of Patent: Jun. 5, 2018

(54) SMALL DIAMETER CARTRIDGE DESIGN FOR A SURGICAL STAPLING INSTRUMENT

(71) Applicant: Covidien LP, Mansfield, MA (US)

(72) Inventor: Sachin Shah, Milford, CT (US)

(73) Assignee: Covidien LP, Mansfield, MA (US)

( * ) Notice: Subject to any disclaimer, the term of this patent is extended or adjusted under 35 U.S.C. 154(b) by 387 days.

(21) Appl. No.: 14/804,711

(22) Filed: Jul. 21, 2015

(65) Prior Publication Data
US 2017/0020525 A1    Jan. 26, 2017

(51) Int. Cl.
| | |
|---|---|
| *A61B 17/04* | (2006.01) |
| *A61B 17/10* | (2006.01) |
| *A61B 17/072* | (2006.01) |
| *A61B 17/068* | (2006.01) |
| *A61B 17/00* | (2006.01) |

(52) U.S. Cl.
CPC .......... *A61B 17/105* (2013.01); *A61B 17/068* (2013.01); *A61B 17/07207* (2013.01); *A61B 2017/0046* (2013.01); *A61B 2017/00473* (2013.01); *A61B 2017/07271* (2013.01); *A61B 2017/07278* (2013.01)

(58) Field of Classification Search
CPC ..... A61B 17/068; A61B 17/105; A61B 17/32; A61B 2090/0801; A61B 2017/2946; A61B 17/8057
USPC .......................................... 227/175.1–182.1
See application file for complete search history.

(56) References Cited

U.S. PATENT DOCUMENTS

| | | | |
|---|---|---|---|
| 3,079,606 | A | 3/1963 | Bobrov et al. |
| 3,490,675 | A | 1/1970 | Green et al. |
| 3,499,591 | A | 3/1970 | Green |
| 3,777,538 | A | 12/1973 | Weatherly et al. |
| 3,882,854 | A | 5/1975 | Hulka et al. |
| 4,027,510 | A | 6/1977 | Hiltebrandt |
| 4,086,926 | A | 5/1978 | Green et al. |
| 4,241,861 | A | 12/1980 | Fleischer |
| 4,244,372 | A | 1/1981 | Kapitanov et al. |
| 4,429,695 | A | 2/1984 | Green |
| 4,505,414 | A | 3/1985 | Filipi |
| 4,520,817 | A | 6/1985 | Green |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

European Search Report dated Jan. 2, 2017, issued in EP Application No. 16180299.

*Primary Examiner* — Robert Long

(57) ABSTRACT

An end effector includes a first jaw, a second jaw, and a cartridge. The first cartridge includes a sled and the second jaw includes an anvil. The first and second jaws are moveable relative to one another. The cartridge is disposed on the first jaw and has a plurality of staples. The sled is configured to engage each staple to the plurality of staples to eject the plurality of staples from the cartridge as the sled is longitudinally translated through the cartridge. A loading unit is also disclosed including an elongated body and an end effector that is articulable relative to the end effector. The end effector and the elongated body of the loading unit are configured to pass or fit through a 5 mm opening.

17 Claims, 9 Drawing Sheets

(56) References Cited

U.S. PATENT DOCUMENTS

| | | |
|---|---|---|
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Sails et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huiterna et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |

(56) References Cited

U.S. PATENT DOCUMENTS

| | | |
|---|---|---|
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicola |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |

(56) References Cited

U.S. PATENT DOCUMENTS

| | | |
|---|---|---|
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |

(56) References Cited

U.S. PATENT DOCUMENTS

| | | |
|---|---|---|
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |

(56) References Cited

U.S. PATENT DOCUMENTS

| | | |
|---|---|---|
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knoclel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |

(56) References Cited

U.S. PATENT DOCUMENTS

| | | |
|---|---|---|
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ulrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |

(56) References Cited

U.S. PATENT DOCUMENTS

| | | |
|---|---|---|
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2* | 9/2014 | Morgan ............... A61B 90/92 227/175.1 |
| 8,840,603 B2 | 9/2014 | Shelton, IV et al. |
| 9,055,941 B2* | 6/2015 | Schmid ............ A61B 17/00491 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0034667 A1 | 2/2007 | Holsten et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0230170 A1* | 9/2009 | Milliman ............ A61B 17/0686 227/176.1 |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277949 A1 | 11/2009 | Viola et al. |
| 2009/0283568 A1 | 11/2009 | Racenet et al. |
| 2009/0308907 A1 | 12/2009 | Nalagatla et al. |
| 2010/0012703 A1 | 1/2010 | Calabrese et al. |
| 2010/0038401 A1* | 2/2010 | Milliman ............ A61B 17/1114 227/175.1 |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0139852 A1* | 6/2011 | Zingman ............ A61B 17/072 227/176.1 |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |

(56) References Cited

U.S. PATENT DOCUMENTS

| | | |
|---|---|---|
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1* | 3/2012 | Schmid ............ A61B 17/07207 227/180.1 |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080500 A1* | 4/2012 | Morgan ................ A61B 90/92 227/179.1 |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1* | 9/2012 | Zemlok ................ A61B 17/072 227/176.1 |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2014/0252068 A1 | 9/2014 | Shelton, IV et al. |
| 2014/0263570 A1 | 9/2014 | Hopkins et al. |
| 2015/0173749 A1 | 6/2015 | Shelton, IV et al. |
| 2015/0238185 A1* | 8/2015 | Schellin ............ A61B 17/07207 227/175.1 |
| 2015/0238187 A1* | 8/2015 | Schellin ............ A61B 17/07207 227/180.1 |

(56) References Cited

U.S. PATENT DOCUMENTS

| | | | | |
|---|---|---|---|---|
| 2015/0297230 | A1* | 10/2015 | Schellin | A61B 17/068 227/176.1 |
| 2015/0366563 | A1* | 12/2015 | Williams | A61B 17/068 227/175.1 |
| 2016/0089143 | A1* | 3/2016 | Harris | A61B 17/068 227/176.1 |

FOREIGN PATENT DOCUMENTS

| | | |
|---|---|---|
| CN | 203898375 U | 10/2014 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A2 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51-149985 | 12/1976 |
| JP | 2001-87272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 08302247 | 7/1983 |
| WO | 89/10094 A1 | 11/1989 |
| WO | 9210976 A1 | 7/1992 |
| WO | 9308754 A1 | 5/1993 |
| WO | 9314706 A1 | 8/1993 |
| WO | 2004/032760 A2 | 4/2004 |
| WO | 2009033057 A2 | 3/2009 |
| WO | 2009071070 A2 | 6/2009 |

\* cited by examiner

SMALL DIAMETER CARTRIDGE DESIGN FOR A SURGICAL STAPLING INSTRUMENT

BACKGROUND

1. Technical Field

The present disclosure relates to surgical instruments and, more specifically, to staple cartridges for surgical stapling instruments having a reduced diameter.

2. Discussion of Related Art

Surgical stapling devices for stapling tissue typically include a tool assembly having a staple cartridge, an anvil, and a knife that can be actuated to effect simultaneous dissection and suturing of tissue. When compared to traditional methods of manually applying threaded sutures to tissue, the use of surgical stapling devices to suture and dissect tissue has increased the speed of the suturing procedure and thus, minimized patient trauma.

In an endoscopic surgical procedure, a surgical stapler is inserted through a small incision in the skin or through a cannula to access a surgical site. Due to the complexity of known surgical stapling devices, a continuing need exists for small diameter surgical stapling devices that are suitable for insertion through smaller diameter openings, e.g., a 5 mm cannula, that can effectively suture and dissect tissue.

SUMMARY

In an aspect of the present disclosure, an end effector includes a first jaw, a second jaw, and a cartridge. The first jaw has a sled and the second jaw has an anvil. The first and second jaws are moveable relative to one another. The cartridge is disposed on the first jaw and has a plurality of staples. The sled is configured to engage each staple of the plurality of staples to eject the plurality of staples from the cartridge as the sled is longitudinally translated through the cartridge. The end effector may have an approximated configuration such that the end effector is configured to fit through a 5 mm opening. The sled may be configured to directly engage each staple of the plurality of staples.

In aspects, the cartridge may define a plurality of vertical slots and a first vertical channel. The lower jaw may define a longitudinal axis with the first vertical channel parallel to the longitudinal axis. The vertical channel may pass through each vertical slot of a first line of the plurality of vertical slots.

In some aspects, a staple of the plurality of staples is disposed in each vertical slot of the plurality of vertical slots. The cartridge and the first jaw may define a sled channel and the sled may be longitudinally translatable through the sled channel. The sled may include a first fin that extends from an upper surface of the sled. The first fin may be translatable through the first vertical channel to engage each staple disposed within the vertical slots of the first line of the plurality of vertical slots.

In certain aspects, each vertical slot of the plurality of vertical slots has a first width transverse to the longitudinal axis and the first vertical channel has a second width transverse to the longitudinal axis. The second width may be less than the first width. The staple of the plurality of staples may be disposed in each vertical slot of the plurality of vertical slots and has a stapled width that is transverse to the longitudinal axis. The staple width may be less than the first width and greater than the second width such that each staple is limited to movement towards and way from a tissue contacting surface of the cartridge. Each staple of the plurality of staples may include legs that are connected by a backspan. The backspan may have a chamfered surface on a proximal end of the backspan. The chamfered surface may be disposed at a chamfer angle relative to a bottom surface of the backspan. The sled may include a first fin and may have a first angled surface that is configured to engage the chamfered surface of each staple of the plurality of staples as the sled is translated through the cartridge. The first angle may be equal to the chamfer angle. The first fin may include a second angled surface that is proximal of the first angled surface. The second angled surface may define a second angle with the upper surface of the sled. The second angle may be greater than the first angle. The second angled surface may be configured to engage the chamfered surface of each staple subsequent to the first angled surface engaging the chamfered surface of each staple.

In another aspect of the present disclosure, a loading unit includes an elongated body and an end effector that is disposed at a distal end of the elongated body. The end effector may be any of the end effectors detailed herein.

In aspects, the elongated body is configured to fit through a 5 mm opening. The end effector may be articulable relative to the elongated body. The elongated body may include a proximal end that is configured to couple the loading unit to a handle. The handle may be manually actuated or electromechanically actuated.

In another aspect of the present disclosure, a method of joining tissue includes clamping tissue between first and second jaws of a surgical instrument and translating a sled through a cartridge of the first jaw. The sled contacting each staple of a plurality of staples to eject the plurality of staples from the cartridge towards the second jaw.

In aspects, translating the sled through the cartridge includes translating the sled through a sled channel that is defined by the first jaw and the cartridge such that a first fin which extends from an upper surface of the sled contacts each of the plurality of staples. Translating the sled through the cartridge may include translating the first fin though a vertical channel and a first line of vertical slots defined by the cartridge. The first line of vertical slots may be disposed along the vertical channel. Contacting each staple of the plurality of staples with the first fin may include contacting a chamfered surface of each staple of the plurality of staples with a first angled surface of the first fin and subsequently contacting the chamfered surface of each staple of the plurality of staples with a second angled surface of the first fin. Contacting the chamfered surface of each staple of the plurality of staples with the first angled surface ejects each staple of the plurality of staples from the cartridge such that legs of the staple penetrate tissue between the first and second jaws. Contacting the chamfered surface of each staple of the plurality of staples with the second angled surface drives the legs of each staple of the plurality of staples into the angle to deform the legs to join the tissue.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1A:
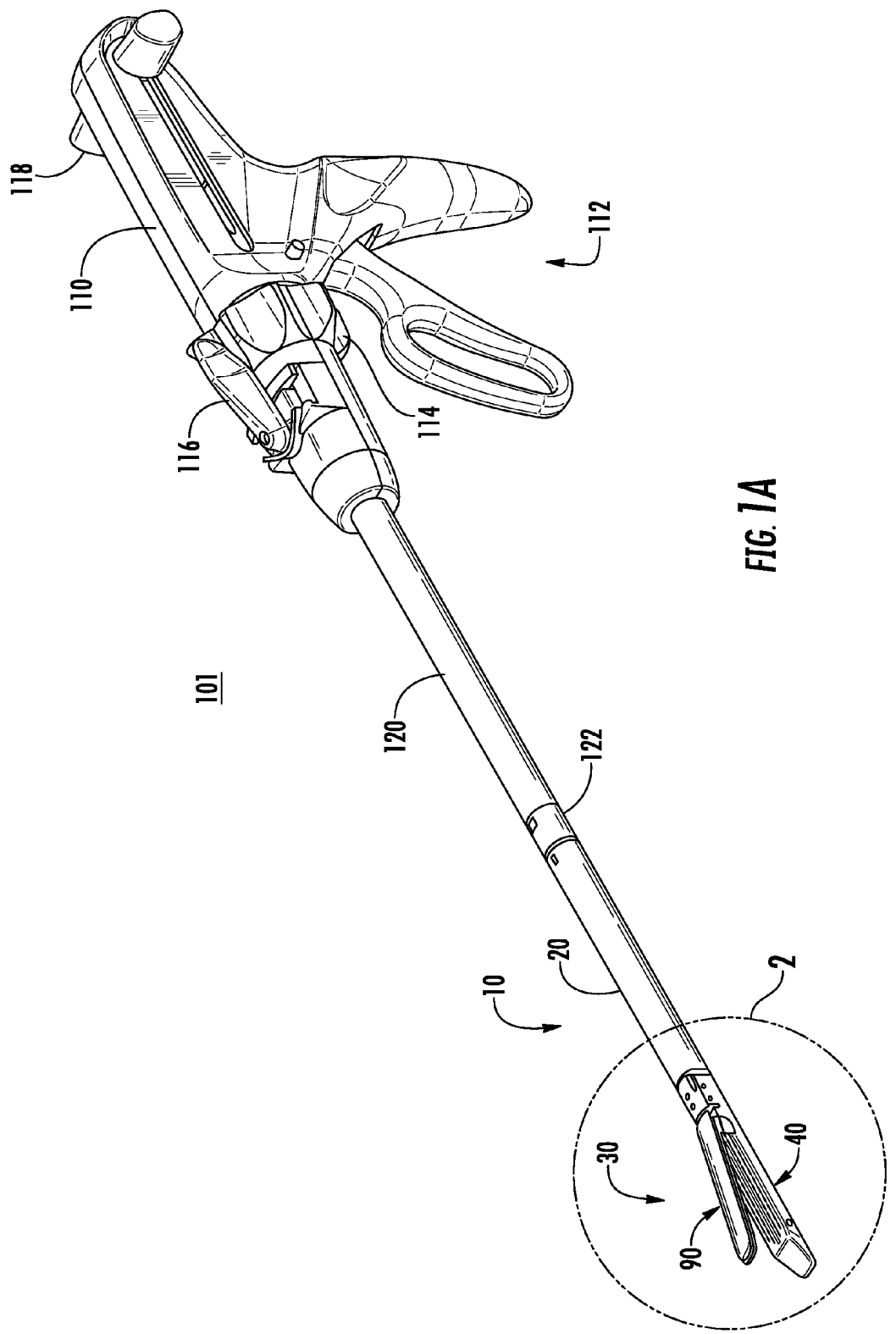
FIG. 1A is a perspective view of a manually actuated surgical instrument and a loading unit provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to a loading unit for joining tissue with staples. The loading unit is sized to fit through a 5 mm opening or port and includes an end effector having upper and lower jaws. The lower jaw has a staple cartridge with a plurality of staples disposed therein. The lower jaw also includes a sled that is translatable through the cartridge such that the sled directly engages each staple to eject the staples from the cartridge and to drive the staples into an anvil of the upper jaw to form the staples.

Figure 1B:
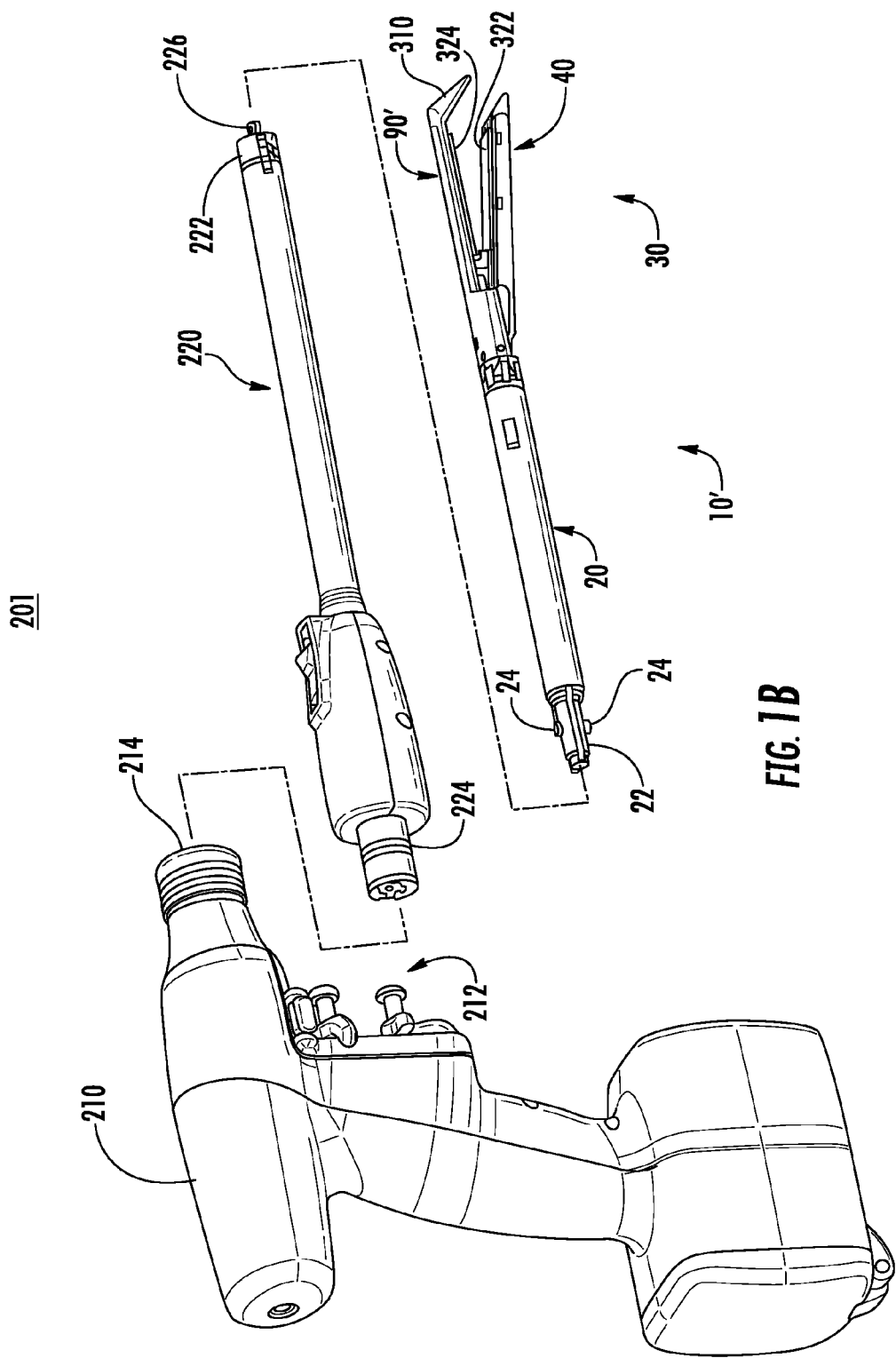
FIG. 1B is a perspective view of a powered surgical instrument and another loading unit provided in accordance with the present disclosure.

Referring now to FIGS. 1A and 1B, a manually actuated surgical instrument 101 and a powered surgical instrument 201 each include a loading unit 10 provided in accordance with the present disclosure. The manually actuated surgical instrument 101 includes a housing 110, a handle assembly 112, a rotation control 114, an actuation lever 116, a retraction control 118, and an elongated portion 120. The elongated portion 120 extends from the housing 110 to support the loading unit 10 at a distal end 122 thereof.

For a detailed description of the structure and function of an exemplary manually actuated surgical instrument reference may be made to U.S. Pat. No. 7,565,993, the entire contents of which are incorporated by reference herein.

The powered surgical instrument 201 includes a powered handle 210 and an adapter 220. The powered handle 210 includes a user interface 212 and an adapter interface 214. The adapter 220 includes a distal end 222 that is configured to support the loading unit 10 and a proximal connector 224 that is configured to be received in the adapter interface 214 of the powered handle 210. For a detailed description of the structure and function of an exemplary powered handle and adapter reference may be made to U.S. Patent Publication No. 2012/0253329, the entire contents of which are incorporated by reference herein.

As seen in FIG. 1B, a loading unit 10' includes an elongated body 20 and an end effector 30. The elongated body 20 includes a connector 22 that releasably couples to the distal end 122 of the elongated portion 120 (FIG. 1A) or the distal end 222 of the adapter 220 (FIG. 1B). The connector 22 includes tabs 24 that align and secure the connector with the elongated portion 120 or the adapter 220. The connector 22 is configured to interface with one or more drive rods, e.g., drive rod 226 of the adapter 226, to actuate one or more functions of the end effector 30 as detailed below. The elongated body 20 of the loading unit 10' may have a diameter of about 5 mm such that the elongated body 20 may fit through a 5 mm cannula or access port. It is also contemplate that the loading unit 10, 10' may be coupled to a robotic surgical system. For a detailed description of the structure and function of an exemplary robotic surgical system reference may be made to U.S. Pat. No. 8,828,023, the entire contents of which are hereby incorporated by reference With continued reference to FIG. 1B, the loading unit 10' includes a dissecting tip 310 on the upper jaw 90'. The dissecting tip 310 is configured to pierce tissue, penetrate tissue, maneuver tissue, or dissect tissue. The dissecting tip 310 may be releasably secured to the upper jaw 90' or may be integrally formed with the upper jaw 90'. For a detailed description of the structure and function of an exemplary dissecting tip reference may be made to U.S. Pat. No. 8,496,153, the entire contents of which are hereby incorporated by reference.

The loading unit 10' may also include a buttress 322 on the lower jaw 40 and/or a buttress 324 on the upper jaw 90'. The buttresses 322, 324 are releasably attached to tissue contacting surfaces of the lower jaw 40 and the upper jaw 90', respectively, to aid in joining tissue together. The buttress 322, 324 may be bioabsorbable and may include medicant to promote healing of tissue joined by the end effector 30. For a detailed description of the structure and function of an exemplary buttress reference may be made to U.S. Pat. No. 8,496,683, the entire contents of which are hereby incorporated by reference.

Figure 2:
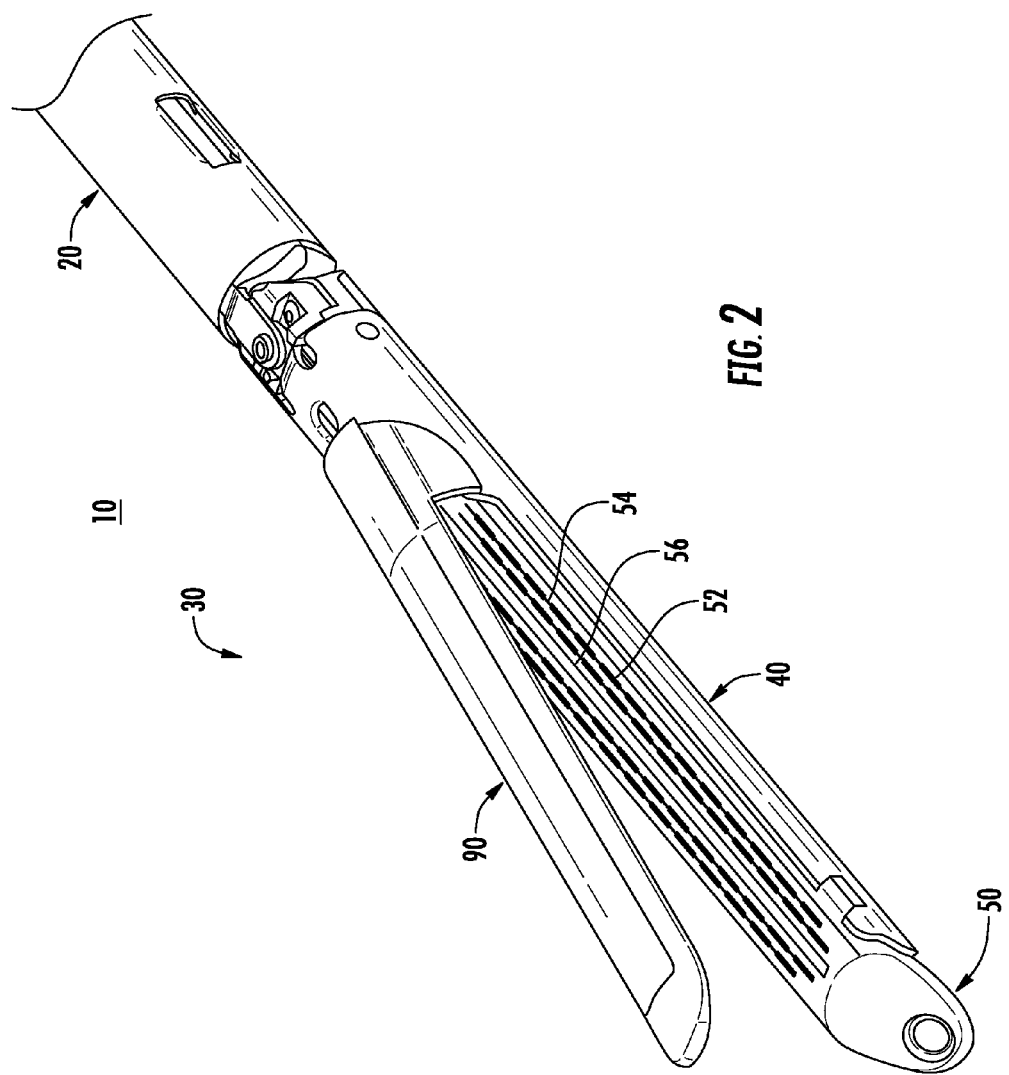
FIG. 2 is an enlarged view of the indicated area of detail of FIG. 1A showing an end effector of the loading unit of FIG. 1A in a spaced-apart configuration.
Figure 3:
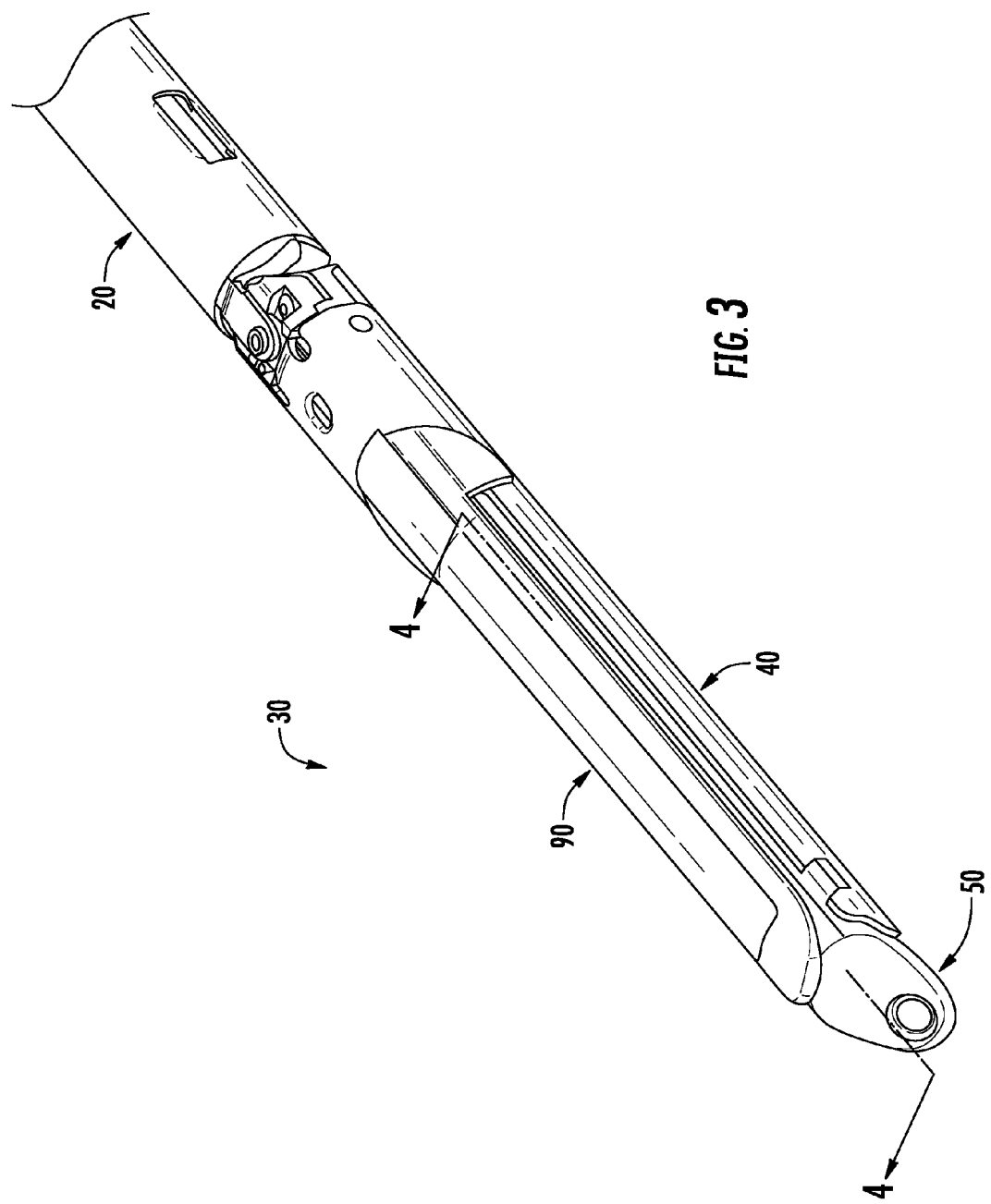
FIG. 3 is a perspective view of the end effector of FIG. 2 in an approximated configuration.
Figure 4:
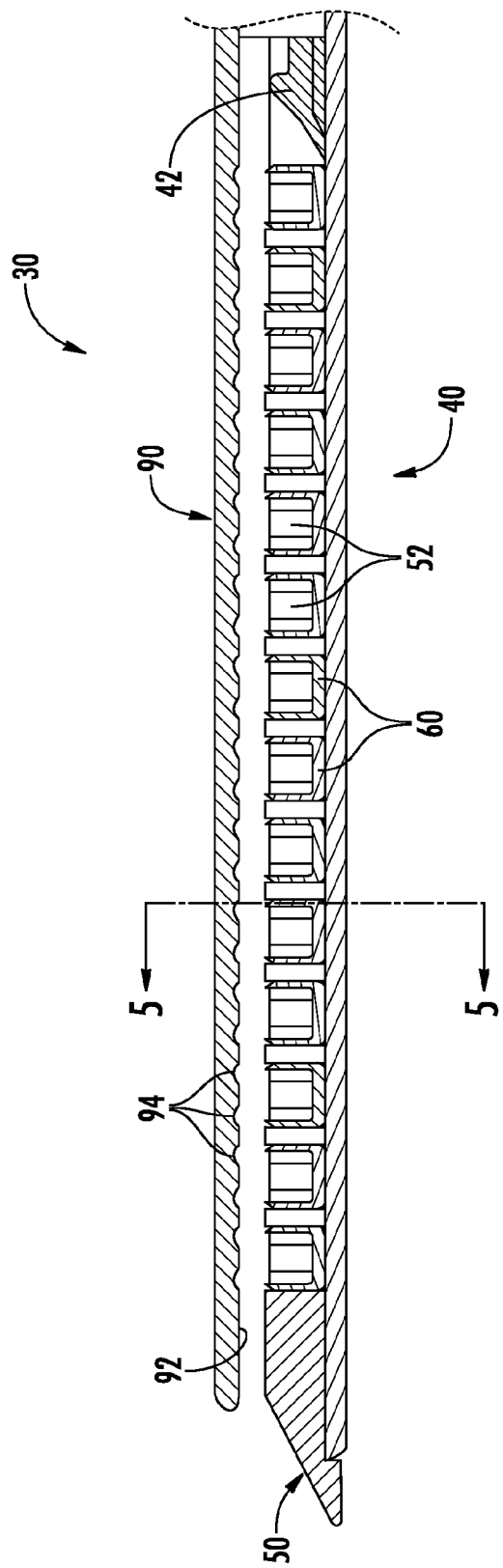
FIG. 4 is a cross-sectional view taken along the section line 4-4 of FIG. 3.

With additional reference to FIGS. 2-4, the end effector 30 includes a first or lower jaw 40 and a second or upper jaw 90 that are moveable relative to one another between a spaced apart configuration (FIG. 2) and an approximated configuration (FIG. 3) to grasp tissue therebetween. In the approximated configuration, the end effector 30 may have a diameter of about 5 mm such that the end effector 30 may fit through a 5 mm cannula or access port. The lower jaw 40 includes a cartridge 50 having a plurality of staples 60 and the upper jaw 90 includes an anvil 92 defining a plurality of staple pockets 94. The cartridge 50 may be releasably coupled to the lower jaw 40. Alternatively, the cartridge 50 may be integrally formed with the lower jaw 40.

With particular reference to FIG. 1A, to actuate the end effector 30 of the loading unit 10 with the manually actuated surgical instrument 101, the proximal end 22 (FIG. 1B) is received in a distal end 122 of the elongated portion 120 to couple the loading unit 10 to the housing 110. Then the handle assembly 112 is actuated to move the end effector 30 to the approximated configuration and to eject staples 60 (FIG. 4) from the cartridge 50 (FIG. 4). Specifically, a moveable handle of the handle assembly 112 is drawn towards a stationary handle of the handle assembly 112 to advance a drive rod (not shown) of the surgical instrument 101 to move the end effector 30 to the approximated configuration. Next, the moveable handle is returned to an unactuated position while the drive rod remains substantially stationary. Then, the moveable handle is actuated a second time to further advance the drive rod which ejects the staples 60 from the cartridge 50 and/or to advance a knife (not explicitly shown), as detailed below.

With particular reference to FIG. 1B, to actuate the end effector 30 of the loading unit 10 with the powered surgical instrument 201, the proximal connector 224 of the adapter 220 is received within the adapter interface 214 of the powered handle 210 to couple the adapter 220 to the powered handle 210. The loading unit 10 is coupled to the adapter 220 by positioning the connector 22 of the loading unit 10 within the distal end 222 of the adapter 220 such that the drive rod 226 of the adapter is received within the connector 22 of the loading unit. The user interface 212 is then manipulated to advance the drive rod 226 which first approximates the end effector 30 and then ejects the staples 60 (FIG. 4) from the cartridge 50 (FIG. 4) as detailed below.

Figure 5:
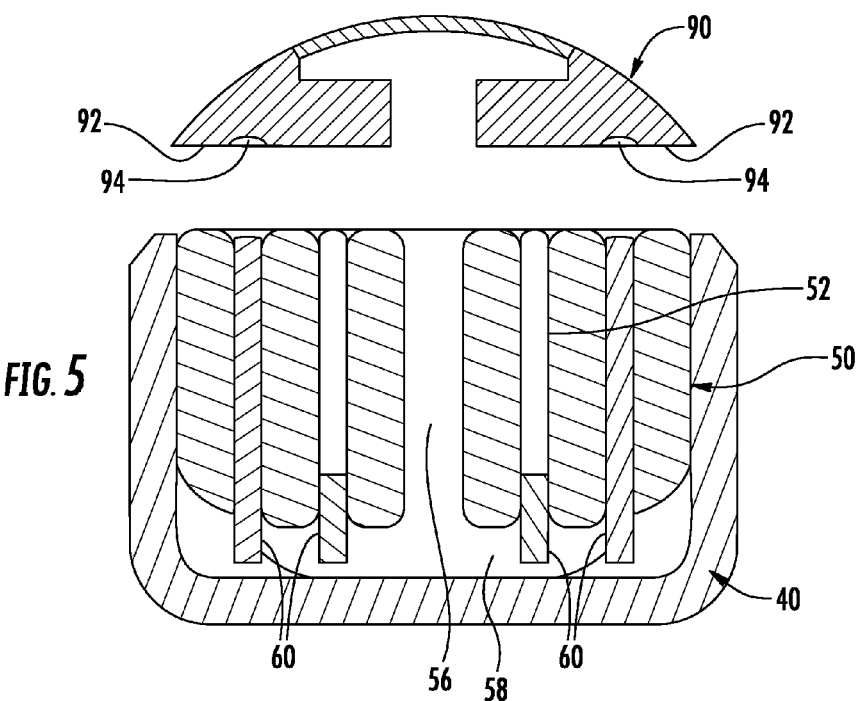
FIG. 5 is a cross-sectional view taken along the section line 5-5 of FIG. 4.
Figure 6:
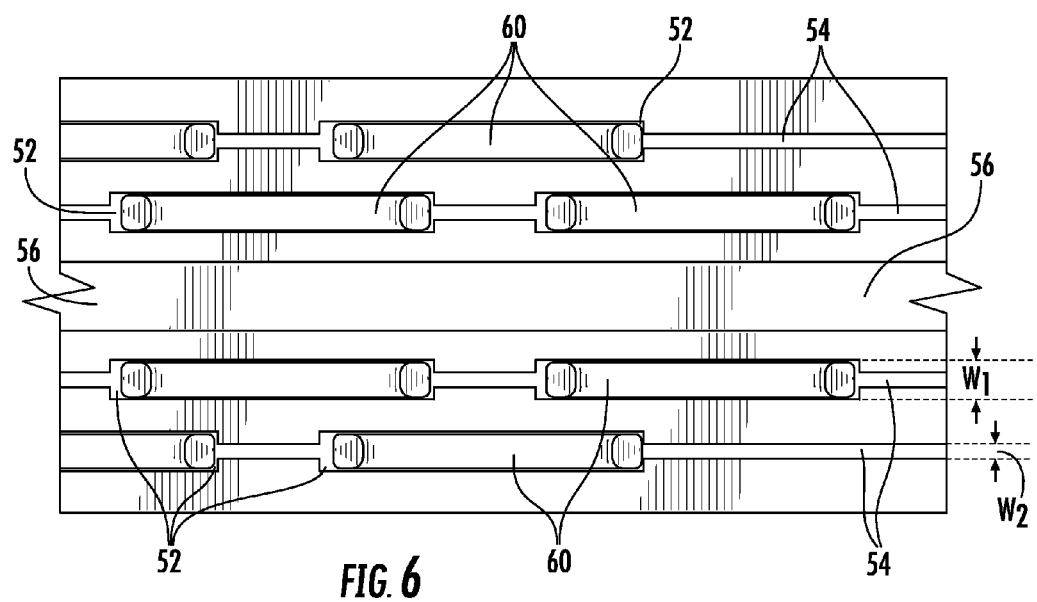
FIG. 6 is a top view of a tissue contacting surface of a cartridge of the end effector of FIG. 2.

Referring to FIGS. 4-6, the cartridge 50 defines a plurality of vertical slots 52, longitudinal vertical channels 54, a longitudinal knife channel 56, and a longitudinal sled channel 58 that passes through a lower portion of each of the vertical slots 52, vertical channels 54, and knife channel 56. The knife channel 56 is disposed along a longitudinal axis of the end effector 30. With particular reference to FIG. 6, the vertical slots 52 are arranged in longitudinal rows which are laterally offset from and parallel to the knife channel 56. Each of the vertical channels 54 passes through one of the longitudinal rows of vertical slots 52. The vertical slots 52 have a first width $W_1$, transverse to the longitudinal axis of the end effector 30, and the vertical channels 54 have a second width $W_2$, transverse to the longitudinal axis of the end effector 30, that is smaller than the first width $W_1$. Each of the vertical slots 52 receives a staple 60 having a width less than the first width $W_1$ and greater than the second width $W_2$ such that each staple 60 is retained within a respective vertical slot 52. Each vertical slot 52 is sized to slidably and releasable retain a staple 60. The vertical channel 54 is sized to receive and guide a fin 44 (FIG. 9) of a sled 42 as the sled 42 is longitudinally translated through the cartridge 50 as detailed below. Further, the fin 44 has a width that is less than a width of the staple 60 as detailed below.

Figure 7:
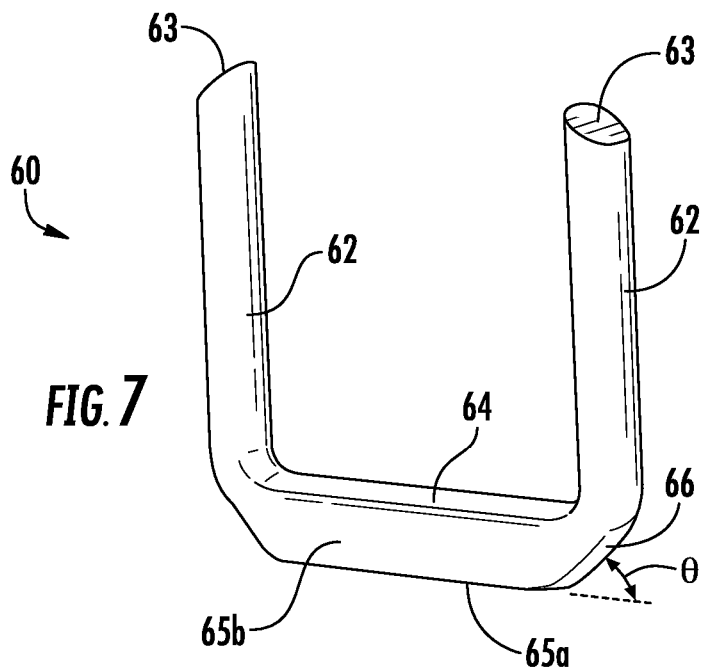
FIG. 7 is a perspective view of a staple of the cartridge of FIG. 6.

With reference to FIG. 7, each staple 60 includes legs 62 joined together by a backspan 64. The legs 62 extend from the backspan 64 to tips 63 which are configured to penetrate tissue. As shown, the tips 63 are angled to penetrate tissue; however, it is contemplated that the tips 63 may have a conical shape or another shape suitable for penetrating tissue. The backspan 64 includes a chamfered surface 66 on at least a proximally facing end when the staple 60 is disposed within a respective vertical slot 52 (FIG. 6). It is contemplated that each end of the backspan 64 may include a chamfered surface 66 as detailed above such that the staples 60 may be positioned in the vertical slots with either end of the backspan 64 facing proximally. The chamfered surface 66 defines a chamfer angle θ with a lower surface 65a of the backspan 64. The chamfer angle θ is in the range of about 5° to about 35° (e.g., about 30°). It is contemplated that each longitudinal row of vertical slots 52 may be sized to receive staples 60 having the same or different dimensions; e.g., length of the legs 62, length of the backspan 64, or width of the legs 62 and backspan 64; from staples 62 of another longitudinal row of vertical slots 52.

In any of the embodiments disclosed herein, the feature on the backspan 64 can be chamfers, rounds, protrusions, one or more bevels, etc., that would engage the sled surface and arranged so that the staple is pushed out of the cartridge.

The backspan 64 of each staple 60 is thicker than a backspan of a traditional staple and functions as a pusher for the respective staple 60. By having the backspan 64 function as a pusher, traditional pushers may be eliminated from the staple cartridge 50 which allows the staple cartridge 50 to have a smaller diameter than a traditional staple cartridge. The backspan 64 is substantially rectangular in cross-section with vertical side surfaces 65b and a length substantially equal to a longitudinal length of a respective vertical slot 52 such that the backspan 64 is configured to guide the staple 60 within the respective vertical slot 52 as detailed below.

Figure 8:
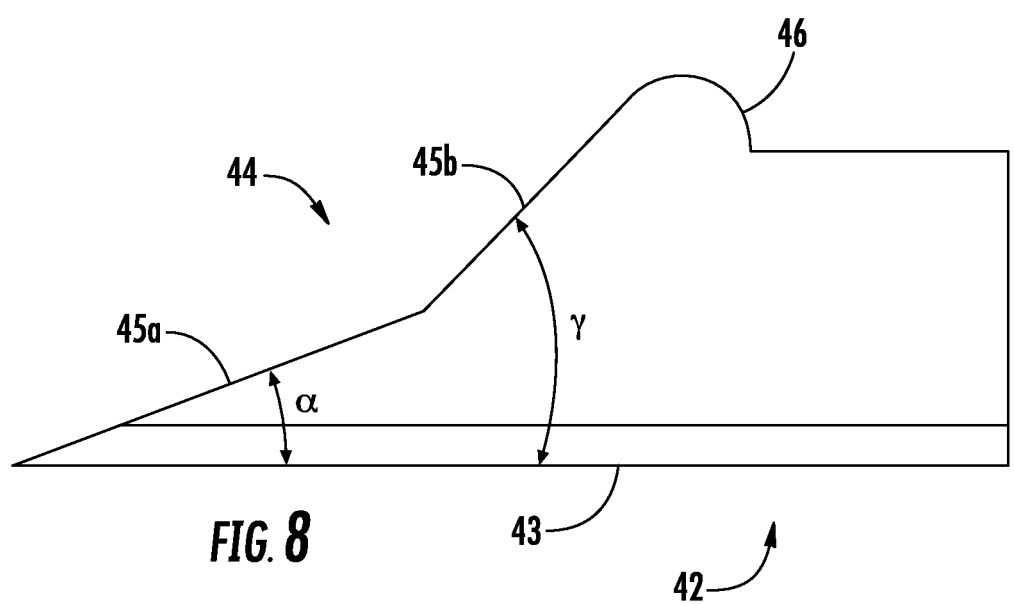
FIG. 8 is a side view of a sled of the end effector of FIG. 4.
Figure 9A:
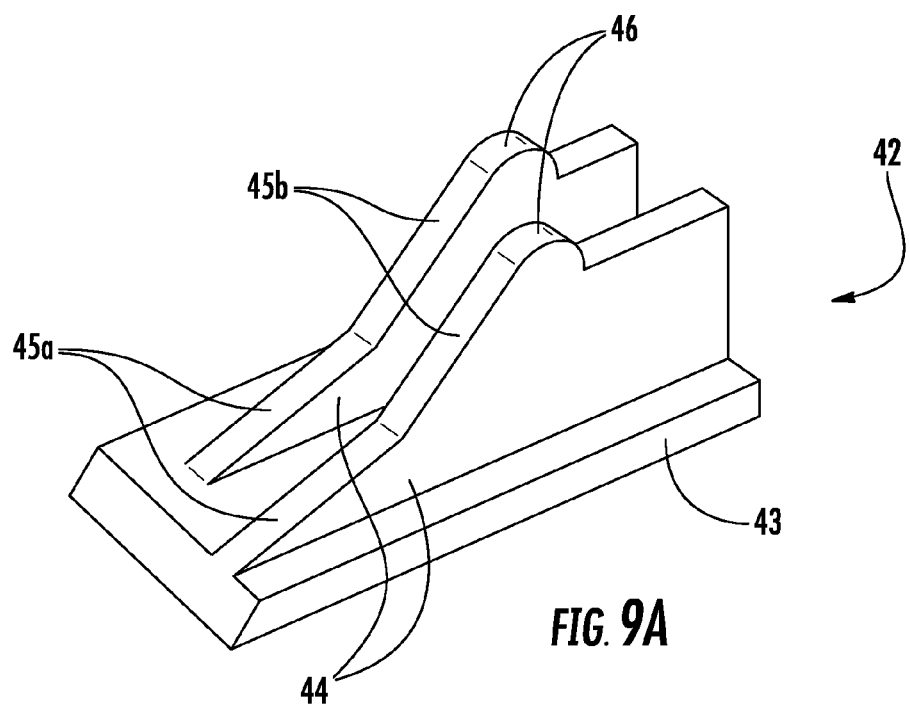
FIG. 9A is a perspective view of the sled of FIG. 8.

Referring briefly back to FIG. 4, the lower jaw 40 includes a sled 42 that is slidable through the sled channel 58 of the cartridge 50 to eject the staples 60 from the cartridge 50. With reference to FIGS. 8 and 9A, the sled 42 includes a horizontal base 43 and one or more fins 44 extending vertically from the base 43. Each fin 44 is slidable through a vertical channel 54 of the cartridge 50 and has a first angled surface 45a and a second angled surface 45b positioned distal to the first angled surface 45a. The first angled surface 45a is substantially linear and defines a first angle α with the base 43 of the sled 42. The second angled surface 45b is substantially linear and defines a second angle γ relative to the base 43 of the sled 42. The first angle α is substantially equal to the chamfer angle θ of the chamfered surface 66 of the backspan 64 of each staple 60. The second angle γ is greater than the first angle α. The first angle α may in a range of about 5° to about 35° (e.g., 30°) and the second angle γ may be in a range of about 25° to about 45° (e.g., about 40°). For a detailed discussion of the sleds with first and second angles reference may be made to U.S. Pat. No. 7,635,074 ("the '074 Patent), the entire contents of which are hereby incorporated by reference.

As shown, the sled 42 is configured to be positioned on one side of the knife channel 56 and the lower jaw 40 may include another sled 42 disposed on either side of the knife channel 56. The sled 42 includes two fins 44 such that as the base 43 translated through the sled channel 58, each fin 44 slides or translates through a respective vertical channel 54 to eject staples 60 positioned within the vertical slots 52 aligned with the respective vertical channel 54. The fins 44 may be longitudinally offset from one another on the base 43 of the sled 42.

Figure 9B:
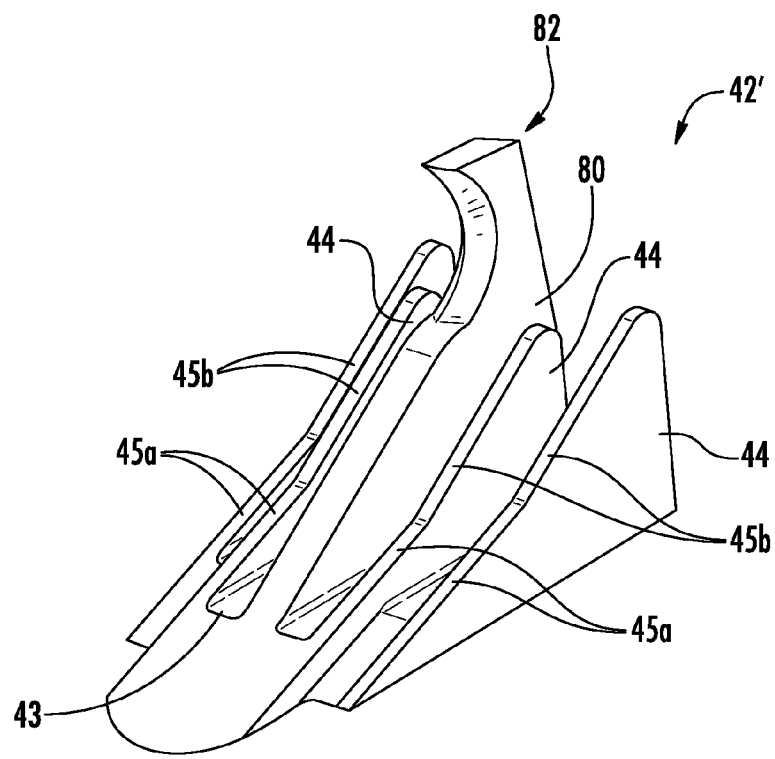
FIG. 9B is a perspective view of another sled in accordance with the present disclosure.

With reference to FIG. 9B, another sled 42' is provided in accordance with the present disclosure. The sled 42' includes a central fin 80 that extends from an upper surface of a base 43 thereof which is sized to slide within the knife channel 56 of the cartridge 50. The central fin 80 may include a knife 82 that extends from an upper surface of the central fin 80 which is configured to sever tissue joined together by the staples 60 as detailed below. The sled 42' also includes fins 44 that extend from the upper surface of a base 43 laterally spaced on from and on both sides of the central fin 80. As detailed above, the fins 44 have first and second angled surfaces 45a, 45b. The fins 44 on each side of the central fin 80 are longitudinally and laterally spaced apart from one another. Examples of such sleds are disclosed in the '074 Patent.

Figure 10:
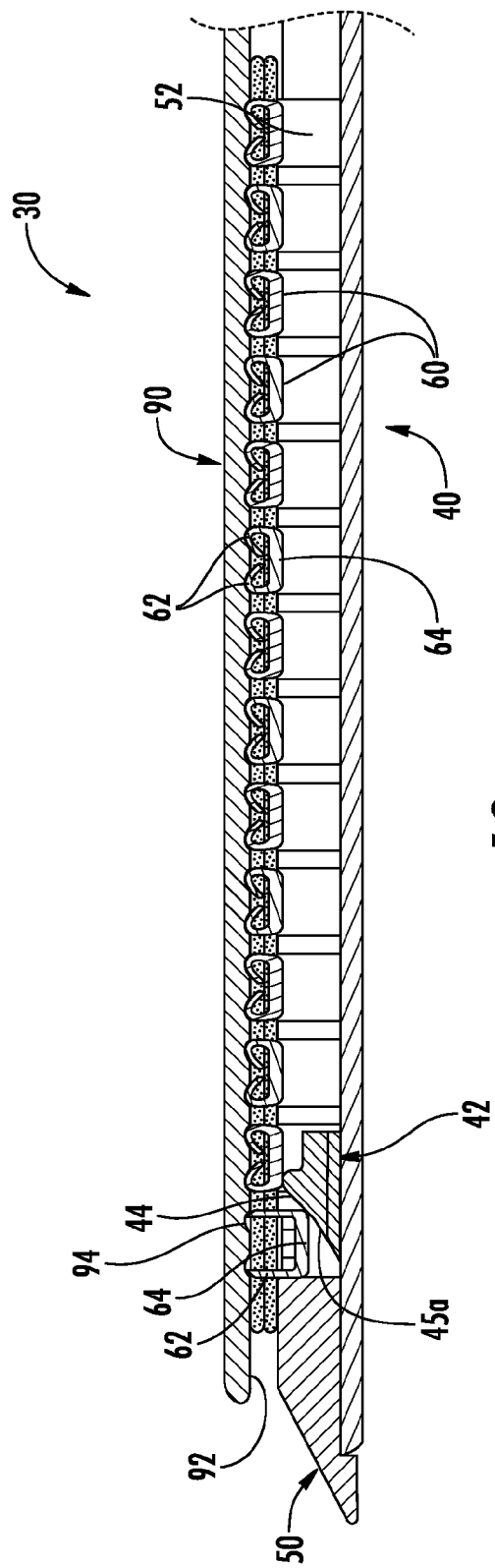
FIG. 10 is a cross-sectional view of the end effector of FIG. 4 with the sled translated through the cartridge to eject the staples from the cartridge.

Referring to FIGS. 4, 7, and 10, a method of joining tissue with the end effector 30 is disclosed in accordance with the present disclosure. The end effector 30 is positioned over tissue in the spaced apart configuration with the tissue positioned between the upper and lower jaws 40, 90. The upper and lower jaws 40, 90 are then approximated to grasp tissue between the upper and lower jaws 40, 90. With tissue grasped between the upper and lower jaws 40, 90, the sled 42 is translated distally through the cartridge 50 such that the fins 44 directly engage the backspans 64 of the staples to eject the staples 60 from the cartridge 50 as shown in FIG. 10. Specifically, the first angled surface 45a of a respective fin 44 engages the chamfered surface 66 of a backspan 64 of a staple 60 to eject the staple 60 from the staple cartridge 50 (i.e., move the staple 60 towards the anvil 92). As the staple 60 is ejected from the staple cartridge 50, the legs 62 of the staple 60 are driven through the tissue grasped between the upper and lower jaws 40, 90 until the tips 63 of the legs 62 engage the staple pockets 94 of the anvil 92 of the upper jaw 90. As the tips 63 engage the staple pockets 94, the second angled surface 45b of the respective fin 44 engages the chamfered surface 66 of the backspan 64 to drive the staple 60 into the anvil 92 such that the legs 62 of the staple 60 are deformed to form the staple 60 (e.g., deform into a B-shape) and join the tissue together.

The backspan 64 of the staple 60 is configured to maintain a substantially parallel relationship with a tissue contacting surface 51 of the staple cartridge 50 as the staple 60 is ejected from the cartridge 50 and driven into the anvil 92. Specifically, as detailed above, the backspan 64 has a substantially rectangular cross-section such that the vertical sides 65b of the backspan 64 slide within the vertical slot 52, and the backspan 64 has a length substantially equal to the vertical slot 52 such that the backspan 64 maintains a horizontal configuration as the staple 60 is ejected from the vertical slot 52. In addition, the legs 62 of the staple 60 may resist deformation adjacent the backspan 64 such that the legs 62 maintain a horizontal configuration of the staple 60 as the staple 60 is ejected from the vertical slot 52.

As the sled 42 is translated through the cartridge 50 to eject the staples 60 from the cartridge 50, a knife (not shown) is translated through the knife slot 56 to sever the tissue grasped between the upper and lower jaws 40, 90 between the inner rows of vertical slots 52. The knife trails the fins 44 of the sled 42 such that the knife severs the tissue after the staples 60 are formed to join the tissue. Such a configuration may reduce bleeding and enhance the severing of tissue as the knife is translated through the knife slot 56.

When the sled 42 reaches an end of the sled channel 58 and all the staples 60 are ejected and formed to join the tissue, the upper and lower jaws 40, 90 are opened to the spaced-apart configuration to release the joined tissue. The end effector 30 is then withdrawn from the surgical site. After the end effector 30 is withdrawn from the surgical site, the loading unit 10 (FIG. 1A) may be detached from the surgical instrument (e.g., surgical instrument 101, 201). With the loading unit 10 separated from surgical instrument, the loading unit 10 may be sterilized for reuse in another surgical procedure and another loading unit 10 may be secured to the surgical instrument to join additional tissue in the manner detailed above. Alternatively, after the loading unit 10 is withdrawn from the surgical site, the cartridge 50 may be detached from the lower jaw 40 and the lower jaw 40 may be reloaded with a new cartridge 50 to join additional tissue in the manner detailed above.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An end effector comprising:
   a first jaw including a sled and defining a longitudinal axis;
   a second jaw including an anvil, the first and second jaws moveable relative to one another; and
   a cartridge disposed on the first jaw and having a plurality of staples, the sled configured to engage each staple of the plurality of staples to eject the plurality of staples from the cartridge as the sled is longitudinally translated through the cartridge, the cartridge defining a plurality of vertical slots and a first vertical channel, the first vertical channel parallel to the longitudinal axis, the first vertical channel passing through each vertical slot of a first line of the plurality of vertical slots.

2. The end effector according to claim 1, wherein the end effector is configured to fit through a 5 mm opening when in an approximated configuration.

3. The end effector according to claim 1, wherein a staple of the plurality of staples is disposed in each vertical slot of the plurality of vertical slots.

4. The end effector according to claim 3, wherein the cartridge and the first jaw define a sled channel, the sled longitudinally translatable through the sled channel.

5. The end effector according to claim 4, wherein the sled includes a first fin extending from an upper surface of the sled, the first fin translatable through the first vertical channel to engage each staple disposed within the vertical slots of the first line of the plurality of vertical slots.

6. The end effector according to claim 1, wherein each vertical slot of the plurality of vertical slots has a first width transverse to the longitudinal axis and the first vertical channel has a second width transverse to the longitudinal axis, the second width being less than the first width.

7. The end effector according to claim 6, wherein a staple of the plurality of staples is disposed in each vertical slot of the plurality of vertical slots and has a staple width, transverse to the longitudinal axis, that is less than the first width and greater than the second width such that each staple is limited to movement towards and away from a tissue contacting surface of the cartridge.

8. The end effector according to claim 7, wherein each staple of the plurality of staples includes legs connected by a backspan, the backspan having a chamfered surface on a proximal end thereof, the chamfered surface disposed at a chamfer angle relative to a bottom surface of the backspan.

9. The end effector according to claim 8, wherein the sled includes a first fin extending from an upper surface of the sled, the first fin having a first angled surface disposed at a first angle relative to the upper surface of the sled, the first angled surface configured to engage the chamfered surface of each staple of the plurality of staples as the sled is translated through the cartridge.

10. The end effector according to claim 9, wherein the first angle is equal to the chamfer angle.

11. The end effector according to claim 10, wherein the first fin includes a second angled surface proximal of the first angled surface, the second angled surface defining a second angle with the upper surface of the sled, the second angle greater than the first angle, the second angled surface configured to engage the chamfered surface of each staple subsequent to the first angled surface engaging the chamfered surface of each staple.

12. A loading unit comprising:
an elongated body having proximal and distal ends; and
an end effector disposed at the distal end of elongated body, the end effector including:
   a first jaw including a sled and defining a longitudinal axis;
   a second jaw including an anvil, the first and second jaws moveable relative to one another; and
   a cartridge disposed on the first jaw and having a plurality of staples, the sled configured to directly engage each staple of the plurality of staples to eject the plurality of staples from the cartridge as the sled is longitudinally translated through the cartridge, the cartridge defining a plurality of vertical slots and a first vertical channel, the first vertical channel parallel to the longitudinal axis, the first vertical channel passing through each vertical slot of a first line of the plurality of vertical slots.

13. The end effector according to claim 12, wherein the elongated body is configured to fit through a 5 mm opening.

14. The end effector according to claim 12, wherein the end effector is articulable relative to the elongated body.

15. A method of joining tissue, the method comprising:
clamping tissue between first and second jaws of a surgical instrument; and
translating a sled through a cartridge of the first jaw, the sled contacting each staple of a plurality of staples to eject the plurality of staples from the cartridge towards the second jaw, the sled translating through a sled channel defined by the first jaw and the cartridge such that a first fin that extends from an upper surface of the sled contacts each staple of the plurality of staples, the first fin translating through a vertical channel and a first line of vertical slots defined by the cartridge, the first line of vertical slots disposed along the vertical channel.

16. The method according to claim 15, wherein contacting each staple of the plurality of staples with the first fin includes contacting a chamfered surface of each staple of the plurality of staples with a first angled surface of the first fin and subsequently contacting the chamfered surface of each staple of the plurality of staples with a second angled surface of the first fin.

17. The method according to claim 16, wherein contacting the chamfered surface of each staple of the plurality of staples with the first angled surface ejects each staple of the plurality of staples from the cartridge such that legs of the staple penetrate tissue between the first and second jaws, and contacting the chamfered surface of each staple of the plurality of staples with the second angled surface drives the legs of each staple of the plurality of staples into an anvil on the second jaw to deform the legs to join the tissue.

* * * * *